US005985348A

United States Patent [19]

Barclay

[11] Patent Number: 5,985,348
[45] Date of Patent: Nov. 16, 1999

[54] MILK PRODUCTS HAVING HIGH CONCENTRATIONS OF OMEGA-3 HIGHLY UNSATURATED FATTY ACIDS

[75] Inventor: William R. Barclay, Boulder, Colo.

[73] Assignee: OmegaTech, Inc., Boulder, Colo.

[21] Appl. No.: 08/918,325

[22] Filed: Aug. 26, 1997

Related U.S. Application Data

[62] Division of application No. 08/483,477, Jun. 7, 1995, Pat. No. 5,698,244.

[51] Int. Cl.$^6$ .................................................. A23C 1/187
[52] U.S. Cl. ................................ 426/580; 426/2; 426/53; 426/635
[58] Field of Search .................................. 426/49, 53, 2, 426/807, 580, 635, 61; 435/134, 243, 946

[56] References Cited

U.S. PATENT DOCUMENTS

| | | |
|---|---|---|
| 3,296,079 | 1/1967 | Griffin . |
| 3,647,482 | 3/1972 | Yueh . |
| 3,667,969 | 6/1972 | Kracauer . |
| 3,908,026 | 9/1975 | Neely et al. . |
| 3,908,028 | 9/1975 | Neely et al. . |
| 3,924,017 | 12/1975 | Lee et al. . |
| 4,304,794 | 12/1981 | Dwivedi et al. . |
| 4,670,285 | 6/1987 | Clandinin et al. . |
| 4,758,438 | 7/1988 | Stroz et al. . |
| 4,792,418 | 12/1988 | Rubin et al. . |
| 5,012,761 | 5/1991 | Oh . |
| 5,130,242 | 7/1992 | Barclay . |
| 5,133,963 | 7/1992 | Ise ........................................ 424/94.61 |
| 5,234,699 | 8/1993 | Yeo . |
| 5,340,594 | 8/1994 | Barclay . |
| 5,340,742 | 8/1994 | Barclay . |
| 5,415,879 | 5/1995 | Oh . |

FOREIGN PATENT DOCUMENTS

| | | |
|---|---|---|
| 0 231 904 A2 | 8/1987 | European Pat. Off. . |
| 58-196068 | 5/1985 | Japan . |
| 58-213613 | 6/1985 | Japan . |
| 60-105471 | 10/1985 | Japan . |
| WO 88/10112 | 12/1988 | WIPO . |
| WO 89/00606 | 1/1989 | WIPO . |
| WO8900606 | 1/1989 | WIPO . |
| WO 91/14427 | 10/1991 | WIPO . |
| WO 92/12711 | 8/1992 | WIPO . |

OTHER PUBLICATIONS

Ainsworth, "Introduction and Keys to Higher Taxa.", pp. 1–7, 1973, in *The Fungi. An Advanced Treatise*, vol. 4B, (G.C. Ainsworth et al. eds., Academic Press).

Bahnweg et al., "A New Approach to Taxonomy of the Thraustochytriales and Labyrinthulales", pp. 131–140, 1986, in *The Biology of Marine Fungi*, (S.T. Moss ed., Cambridge University Press).

Bartnicki–Garcia, "The Cell Wall: A Crucial Structure in Fungal Evolution", pp. 389–403, 1988, in *Evolutionary Biology of the Fungi*, (A.D.M. Rayner et al. eds., Cambridge University Press).

Behrens et al., "Eicosapentaenoic Acid from Microalgae", p. 623, col. 2, abstract No. 193025d, 1989, Chemical Abstracts, vol. 111, No. 21, Nov. 20.

Cavalier–Smith, "The Origin of Nuclei and of Eukaryotic Cells", pp. 463–468, 1975, *Nature*, vol. 256.

Cerda–Olmeda et al., "A Biography of Phycomyces", pp. 7–26, 1987, in *Phycomyces*, (Cerda–Olmeda et al. eds., CSH Laboratory).

Couch et al., 1973, *Lipids*, 8(7):385–392.

Cruickshank, 1934, "Studies in Fat Metabolism in the Fowl" in *Biochem. J.*, 28:965–977.

Dick, "Saprolegniales", pp. 113–144, 1973, in *The Fungi. An Advanced Treatise*, (G.C. Ainsworth et al. eds., Academic Press)).

Ellenbogen, "Polyunsaturated Fatty Acids of Aquatic Fungi: Possible Phylogenetic Significance", pp. 805–811, 1969, *Comp. Biochem. Physiol.*, vol. 29.

Emerson, "Current Trends of Experimental Research in the Aquatic Phycomycetes", pp. 169–200, 1950, *Ann. Rev. Micro.*, vol. 4.

Erwin, "Comparative Biochemistry of Fatty Acids in Eukaryotic Microorganisms", pp. 41–143, 1973, in *Lipids and Biomembranes of Eukaryotic Microorganisms*, (J. Erwin ed., Academic Press.

Findlay et al., "Biochemical Indicators of the Role of Fungi and Thraustrochytrids in Mangrove Detrital Systems", pp. 91–103, 1986, in *The Biology of Marine Fungi*, (S.T. Moss ed., Cambridge University Press).

Fisher et al., 1957, *J. Nutr.*, 63:119–129.

Fuller, et al., "Isolation and Pure Culture Study of Marine Phycomycetes", pp. 745–756, 1964, *Mycologia*, vol. 56.

Gellerman et al., "Methyl–Directed Desaturation of Arachidonic to Eicosapentaenoic Acid in the Fungus, Saprolegnia Parasitica", pp. 23–30, 1979, *Biochim. Biophys. Acta*, vol. 573.

Goldstein, "Development and Nutrition of New Species of Thraustochystrium", pp. 271–279, 1963, *Am. J. Bot.*, vol. 50.

Goldstein et al., "Biology of a Problematic Marine Fungus, Dermocystidium sp. II. Nutrition and Respiration", pp. 468–472, 1969. *Mycologia*, vol. 61.

(List continued on next page.)

*Primary Examiner*—Anthony J. Weier
*Attorney, Agent, or Firm*—Sheridan Ross P.C.

[57] ABSTRACT

A process for the heterotrophic or predominantly heterotrophic production of whole-celled or extracted microbial products with a high concentration of omega-3 highly unsaturated fatty acids, producible in an aerobic culture under controlled conditions using biologically pure cultures of heterotrophic single-celled fungi microorganisms of the order Thraustochytriales. The harvested whole-cell microbial product can be added to processed foods as a nutritional supplement, or to fish and animal feeds to enhance the omega-3 highly unsaturated fatty acid content of products produced from these animals. The lipids containing these fatty acids can also be extracted and used in nutritional, pharmaceutical and industrial applications.

23 Claims, No Drawings

OTHER PUBLICATIONS

Goldstein et al., "Biology of a Problematic Marine Fungus, Dermocystidium sp. I. Development and Cytology", pp. 1–11, 1966, *Archiv for Mikrobiologie*, vol. 53.1.

Henderson et al., "Lipid Compostion and Biosynthesis in the Marine Dinoflagellate *Crypthecodinium cohnii*", pp. 1679–1683, 1988, *Phytochemistry*, vol. 27. No. 6.

Hori et al., "The Nucleotide Sequence of 5S rRNA from a Cellulai Slime Mold Dictyostelium Discoideum", pp. 5535–5539, 1980, *Nucl. Acids Res.*, vol. 8.

Hunter, "Fish Oil and Other Omega–3 Sources", pp. 1592–1596, 1987, *J. Am. Oil. Chem. Soc.*, vol. 64.

Jong et al., "American Type Culture Collection Catalogue of Fungi/Yeast", pp. 350 and 378, *American Type Culture Collection*, 17th Edition, 1987.

Kates, "Techniques of Lipidology: Isolation, Analysis and Identification of Lipids", pp. 186–278, 1986, *Laboratory Techniques in Biochemistry and Molecular Biology*, vol. 3.

Kyle, "Microalgae as a Source of EPA–Containing Oils", p. 1251, 1987, *J. Am. Oil. Chem. Soc.*, vol. 64.

Lepage et al., "Improved Recovery of Fatty Acid Through Direct Transesterification Without Prior Extraction or Purification", pp. 1391–1396, 1984, *J. Lipid. Res.*, vol. 25.

Lipstein et al., "The Nutritional and Economic Value of Algae for Poultry" in *Algae Biomass*, G. Sheief and C.J. Soeder, eds., Elsevier/North Holland Biomedical Press, 1980, pp. 667–685.

Lipstein et al., 1980, *Br. Poultry Sci.*, 21:9–21.

Mannella et al., "Interrelatedness of 5S RNA Sequences Investigated by Correspondence Analysis", pp. 228–235, 1987, *J. Mol. Evol.*, vol. 24.

Miller, "Isolation and Pure Culture of Aquatic Phycomycetes by Membrane Filtration", pp. 524–527, 1967, *Mycologia*, vol. 59.

Moss, "Biology and Phylogeny of the Labrinthulales and Thraustochytriales", pp. 105–129, 1986, in *The Biology of Marine Fungi*, (S.T. Moss ed., Cambridge Univerisity Press).

Murty et al., 1961, *J. Nutrition*, 75:287–294.

Navarro et al., 1972, *J. Sci. Fd. Agric.*, 23:1287–1292.

Perkins, "Phylogenetic Considerations of the Problematic Thraustochytriaceous–Labrinthulid–Dermocystidium Complex Based on Observations of Fine Structure", pp. 45–63, 1974, *Veroff. Inst. Meeresforsch. Bremerh. Suppl.*, vol. 5.

Pigot, "The Need to Improve Omega–3 Content of Cultured Fish", pp. 63–68, 1989, *World Aquaculture*, vol. 20.

Pohl et al., "Fatty Acids and Lipids of Marine Algae and the Control of Their Biosynthesis by Enviromental Factors", pp. 473–523, 1979, *Marine Algae in Pharmaceutical Science*, (Hoppe et al. eds.).

Reiser, 1951, *J. Nutrition*, 44:159–175.

Ryther, "Cultivation of Macroscopic Marine Algae", pp. 79–88, 1983, *Solar Energy Research Institute Aquatic Species Program Review.* Proc of the Mar. 1983 Principal Investigators Meeting, SERI/CP/–231 1946.

Schlenk, "Urea Inclusion Compounds of Fatty Acids", pp. 243–267, 1954, *Prog. Chem. Fats and Other Lipids*, vol. 2.

Schneider, "Cultivation of Micro–organisms. Section 3.2: Fungi", pp. 337–345, 1976, in *Marine Ecology*, vol. 3, Part 1. *Cultivation*, (O. Kinne ed., Wiley and Sons).

Simopoulos et al. (eds.), *Health Effects of Polyunsaturated Fatty Acids in Seafoods*, Chaps. 2–5, 7, 17, 1986, Academic Press).

Sorokin, "Dry Weight, Packed Cell Volume and Optical Density", pp. 321–343, 1973 in *Handbood of Phycological Methods: Culture Methods and Growth Measurements*, (J.R. Stein ed., Cambridge University Press).

Sparrow, *Aquatic Phycomycetes*, pp. 36–39, 1960, University of Michigan Press.

Wassef, "Fungal Lipids", pp. 159–232, 1977, *Adv. Lipid Res.*, vol. 15.

Weete, "Fatty Acids", pp. 49–95, 1980, in *Lipid Biochemistry of Fungi and Other Organisms*, (Plenum Press).

Yamada et al., "Production of Arachidonic Acid and Elcosapentaenoic Acid by Microorganisms", p. 1254, 1987, *J. Am. Oil Chem. Soc.*, vol. 64.

Akimoto et al., "Metal Salts Requisite for the Production of Elcosapentaenoic Acid by a Marine Bacterium Isolated from Mackerel Intestines", pp. 504–508, 1991, *JAOCS*, vol. 68, Jul.

Ando et al., "Incorporation of n–3 Polyunsatured Fatty Acids into Phospholipids of a Marine Bacterium Vibrio sp. Cultivated with Sardine Oil", pp. 169–171, 1992, *J. Ferm. Bioeng.*, vol. 73.

Bajpai et al., "Production of Docosahexaenoic Acid by *Thraustochytrium aureum*", pp. 706–710, 1991, *Appl. Microbiol. Biotechnol.*, vol. 35.

Bajpai et al., "Effects of Aging Mortierella Mycelium on Production of Arachidonic and Eicosapentaenoic Acids", pp. 775–780, 1991, *JAOCS*, vol. 68, Oct.

Bajpai et al., Optimization of Production of Docosahexaenoic Acid (DHA) by *Thraustochytrium aureum* ATCC 34304, pp. 509–514, 1991, *JAOCS*, vol. 68, Jul.

Bajpai et al., "Eicosapentaenoic Acid (EPA) Formation; Comparative Studies with Mortierella Strains and Production by *Mortierella elongata*", pp. 1294–1298, 1991, *Mycol. Res.*, vol. 95.

Boswell et al., "SCO Production by Fermentative Microalgae", pp. 274–286, 1992, in *Industrial Applications of Single Cell Oils* (Kyle et al., eds.), American Oil Chemists' Society, Champaign, IL.

Cohen et al., "Overproduction of γ–Licolenic and Eicosapentaenoic Acids by Algae", pp. 569–572, 1992, *Plant Physiol.*, vol. 98.

Gandhi et al., Production of the Polyunsaturated Fatty Acids Arachidonic Acid and Eicosapentaenoic Acid by the Fungus *Pythium ultimum*, pp. 1825–1830; 1991, *J. Gen. Microbiol.*, vol. 137.

Hansen et al., Effects of Culture Conditions on Accumulation of Arachidonic and Eicosapentaenoic Acids in Cultured Cells of *Rhytidiadelphus squarrosus* and *Eurhynchium striatum*, pp. 1837–1841, 1991, *Phytochemistry*, vol. 30.

Kendrick et al., "Microbial Polyunsaturated Fatty Acids of Potential Commercial Interest", pp. 59–65, 1992, *SIM Industrial Microbiology NEWS*, vol. 42.

Kendrick et al., "Lipids of Selected Molds Grown for Production of n–3 and n–6 Polyunsaturated Fatty Acids", pp. 15–20, 1992, *LIPIDS*, vol. 27.

Kyle et al., "Bioproduction of Docosahexaenoic Acid (DHA) by Microalgae", pp. 287–300, 1992, in *Industrial Applications of Single Cell Oils* (Kyle et al., eds.), American Oil Chemists' Society, Champaign, IL.

Kyle et al., "Microalgae as a Source of EOA–Containing Oils", pp. 117–121, 1988, *Proc. World Conf. Biotechnol. Fats Oils Ind.*

Radwan, "Sources of $C_{20}$–Polyunsatured Fatty Acids for Biotechnical Use", pp. 421–430, 1991, *Appl. Microbiol. Biotechnol.*, vol. 35.

Yazawa et al., "Production of Eicosapentaenoic Acid from Marine Bacteria", pp. 29–51, 1992, in *Industrial Applications of Single Cell Oils* (Kyle et al., eds.), American Oil Chemists' Society, Champaign, IL.

Yongmanitchai et al., "Screening of Algae for Potential Alternative Sources of Eicosapentaenoic Acid", pp. 2963–2967, 1991, *Phytochemistry*, vol. 30.

Yamada et al., "Production of Dihomo–γ–Linolenic Acid, Arachidonic Acid and Eicosapentaenoic Acid by Filamentous Fungi", pp. 118–138, 1992, in *Industrial Applications of Single Cell Oils* (Kyle et al., eds.), American Oil Chemists' Society, Champaign, Il.

Yongmanitchai et al., "Omega–3 Fatty Acids: Alternative Sources of Production", pp. 117–125, 1989, *Proc. Biochem.*

STN Database, AN 88:13222 Biobusiness for Milchwissenschaft, vol. 43, No. 3, pp. 153, 155–158 Author:Hagemeister et al, Mar. 1988.

STN Database, AN 89:532569 Caplus for WO 88–US2483 Author: T. Long, Jul. 1988.

STN Database, AN 69:410511 Caplus for Comp. Biochem. Physiol., 29(2) pp. 805–811, Author: Ellenbogen et al, Feb. 1969.

MILK PRODUCTS HAVING HIGH CONCENTRATIONS OF OMEGA-3 HIGHLY UNSATURATED FATTY ACIDS

CROSS-REFERENCE TO RELATED APPLICATIONS

This application is a divisional of U.S. application Ser. No. 08/483,477, filed Jun. 7, 1995, now U.S. Pat. No. 5,698,244. The following are related patents and applications which are incorporated by reference herein in their entirety; however, priority is not claimed from the following related patents and applications: U.S. patent application Ser. No. 08/292,736, filed Aug. 18, 1994, now U.S. Pat. No. 5,656,319, issued Aug. 12, 1997, which is a divisional application of U.S. patent application Ser. No. 07/911,760, filed Jul. 10, 1992, now U.S. Pat. No. 5,340,594, issued Aug. 23, 1994, which is a divisional application of U.S. patent application Ser. No. 07/580,778, filed Sep. 11, 1990, now U.S. Pat. No. 5,130,242, issued Jul. 14, 1992, which is a continuation-in-part application of U.S. patent application Ser. No. 07/439,093, filed Nov. 17, 1989, now abandoned, which is a continuation-in-part of U.S. patent application Ser. No. 07/241,410, filed Sep. 7, 1988, now abandoned.

FIELD OF THE INVENTION

The present invention concerns a method for raising an animal having with high concentrations of omega-3 highly unsaturated fatty acids (HUFA) and food products derived from such animals.

BACKGROUND OF THE INVENTION

Omega-3 highly unsaturated fatty acids are of significant commercial interest in that they have been recently recognized as important dietary compounds for preventing arteriosclerosis and coronary heart disease, for alleviating inflammatory conditions and for retarding the growth of tumor cells. These beneficial effects are a result both of omega-3 highly unsaturated fatty acids causing competitive inhibition of compounds produced from omega-6 fatty acids, and from beneficial compounds produced directly from the omega-3 highly unsaturated fatty acids themselves (Simopoulos et al., 1986). Omega-6 fatty acids are the predominant highly unsaturated fatty acids found in plants and animals. Currently the only commercially available dietary source of omega-3 highly unsaturated fatty acids is from certain fish oils which can contain up to 20–30% of these fatty acids. The beneficial effects of these fatty acids can be obtained by eating fish several times a week or by daily intake of concentrated fish oil. Consequently large quantities of fish oil are processed and encapsulated each year for sale as a dietary supplement.

However, there are several significant problems with these fish oil supplements. First, they can contain high levels of fat-soluble vitamins that are found naturally in fish oils. When ingested, these vitamins are stored and metabolized in fat in the human body rather than excreted in urine. High doses of these vitamins can be unsafe, leading to kidney problems or blindness and several U.S. medical associations have cautioned against using capsule supplements rather than real fish. Secondly, fish oils contain up to 80% of saturated and omega-6 fatty acids, both of which can have deleterious health effects. Additionally, fish oils have a strong fishy taste and odor, and as such cannot be added to processed foods as a food additive, without negatively affecting the taste of the food product. Moreover, the isolation of pure omega-3 highly unsaturated fatty acids from this mixture is an involved and expensive process resulting in very high prices ($200–$1000/g) for pure forms of these fatty acids (Sigma Chemical Co., 1988; CalBiochem Co., 1987).

The natural source of omega-3 highly unsaturated fatty acids in fish oil is algae. These highly unsaturated fatty acids are important components of photosynthetic membranes. Omega-3 highly unsaturated fatty acids accumulate in the food chain and are eventually incorporated in fish oils. Bacteria and yeast are not able to synthesize omega-3 highly unsaturated fatty acids and only a few fungi are known which can produce minor and trace amounts of omega-3 highly unsaturated fatty acids (Weete, 1980; Wassef, 1977; Erwin, 1973).

Thus, until the present invention, there have been no known heterotrophic organisms suitable for culture that produce practical levels of omega-3 highly unsaturated fatty acids or methods for incorporation of such omega-3 highly unsaturated fatty acids into human diets.

BRIEF SUMMARY OF THE INVENTION

One embodiment of the present invention relates to a method of raising an animal comprising feeding the animal Thraustochytriales or omega-3 HUFAs extracted therefrom. Animals raised by the method of the present invention include poultry, cattle, swine and seafood, which includes fish, shrimp and shellfish. The omega-3 HUFAs are incorporated into the flesh, eggs and milk products. A further embodiment of the invention includes such products.

DETAILED DESCRIPTION OF THE INVENTION

For purposes of definition throughout the application, it is understood herein that a fatty acid is an aliphatic monocarboxylic acid. Lipids are understood to be fats or oils including the glyceride esters of fatty acids along with associated phosphatides, sterols, alcohols, hydrocarbons, ketones, and related compounds.

A commonly employed shorthand system is used in this specification to denote the structure of the fatty acids (e.g., Weete, 1980). This system uses the letter "C" accompanied by a number denoting the number of carbons in the hydrocarbon chain, followed by a colon and a number indicating the number of double bonds, i.e., C20:5, eicosapentaenoic acid. Fatty acids are numbered starting at the carboxy carbon. Position of the double bonds is indicated by adding the Greek letter delta (D) followed by the carbon number of the double bond; i.e., C20:5omega-3$D^{5,8,11,14,17}$. The "omega" notation is a shorthand system for unsaturated fatty acids whereby numbering from the carboxy-terminal carbon is used. For convenience, w3 will be used to symbolize "omega-3," especially when using the numerical shorthand nomenclature described herein. Omega-3 highly unsaturated fatty acids are understood to be polyethylenic fatty acids in which the ultimate ethylenic bond is 3 carbons from and including the terminal methyl group of the fatty acid. Thus, the complete nomenclature for eicosapentaenoic acid, an omega-3 highly unsaturated fatty acid, would be C20:5w3$D^{5,8,11,14,17}$. For the sake of brevity, the double bond locations ($D^{5,8,11,14,17}$) will be omitted. Eicosapentaenoic acid is then designated C20:5w3, Docosapentaenoic acid (C22:5w3$D^{7,10,13,16,19}$) is C22:5w3, and Docosahexaenoic acid (C22:6w3$D^{4,7,10,13,16,19}$) is C22:6w3. The nomenclature "highly unsaturated fatty acid" means a fatty acid with 4 or more double bonds. "Saturated fatty acid" means a fatty acid with 1 to 3 double bonds.

A collection and screening process has been developed to readily isolate many strains of microorganisms with the following combination of economically desirable characteristics for the production of omega-3 highly unsaturated fatty acids: 1) capable of heterotrophic growth; 2) high content of omega-3 highly unsaturated fatty acids; 3) unicellular; 4) preferably low content of saturated and omega-6 highly unsaturated fatty acids; 5) preferably nonpigmented, white or essentially colorless cells; 6) preferably thermotolerant (ability to grow at temperatures above 30° C.); and 7) preferably euryhaline (able to grow over a wide range of salinities, but especially at low salinities).

Collection, isolation and selection of large numbers of suitable heterotrophic strains can be accomplished according to the method disclosed in related U.S. Pat. No. 5,340,594, issued Aug. 23, 1994, which is incorporated herein by this reference in its entirety.

It has been unexpectedly found that species/strains from the genus Thraustochytrium can directly ferment ground, unhydrolyzed grain to produce omega-3 HUFAs. This process is advantageous over conventional fermentation processes because such grains are typically inexpensive sources of carbon and nitrogen. Moreover, practice of this process has no detrimental effects on the beneficial characteristics of the algae, such as levels of omega-3 HUFAs.

The present process using direct fermentation of grains is useful for any type of grain, including without limitation, corn, sorghum, rice, wheat, oats, rye and millet. There are no limitations on the grind size of the grain. However, it is preferable to use at least coarsely ground grain and more preferably, grain ground to a flour-like consistency. This process further includes alternative use of unhydrolyzed corn syrup or agricultural/fermentation by-products such as stillage, a waste product in corn to alcohol fermentations, as an inexpensive carbon/nitrogen source.

In another process, it has been found that omega-3 HUFAs can be produced by Thraustochytrium or Schizochytrium by fermentation of above-described grains and waste products which have been hydrolyzed. Such grains and waste products can be hydrolyzed by any method known in the art, such as acid hydrolysis or enzymatic hydrolysis. A further embodiment is a mixed hydrolysis treatment. In this procedure, the ground grain is first partially hydrolyzed under mild acid conditions according to any mild acid treatment method known in the art. Subsequently, the partially hydrolyzed ground grain is further hydrolyzed by an enzymatic process according to any enzymatic process known in the art. In this preferred process, enzymes such as amylase, amyloglucosidase, alpha or beta glucosidase, or a mixture of these enzymes are used. The resulting hydrolyzed product is then used as a carbon and nitrogen source in the present invention.

Using the collection and screening process outlined above, strains of unicellular fungi and algae can be isolated which have omega-3 highly unsaturated fatty acid contents up to 32% total cellular ash-free dry weight (afdw), and which exhibit growth over a temperature range from 15–48° C. and grow in a very low salinity culture medium. Many of the very high omega-3 strains are very slow growers. Stains which have been isolated by the method outlined above, and which exhibit rapid growth, good production and high omega-3 highly unsaturated fatty acid content, have omega-3 unsaturated fatty acid contents up to approximately 10% afdw.

Growth of the strains by the invention process can be effected using the methods disclosed in U.S. Pat. No. 5,340,594 issued Aug. 23, 1994, which is incorporated herein by this reference in its entirety, and the methods disclosed in WO 94/08467 published on Apr. 28, 1994, which is incorporated herein by this reference in its entirety. The unicellular strains of heterotrophic microorganisms isolated by the screening procedure outlined above, tend to have high concentrations of three omega-3 highly unsaturated fatty acids: C20:5w3, C22:5w3 and C22:6w3 and very low concentration of C20:4w6. The ratios of these fatty acids can vary depending on culture conditions and the strains employed. Ratios of C20:5w3 to C22:6w3 can run from about 1:1 to 1:30. Ratios of C22:5w3 to C22:6w3 can run from 1:12 to only trace amounts of C22:5w3. In the strains that lack C22:5w3, the C20:5w3 to C22:6w3 ratios can run from about 1:1 to 1:10. An additional highly unsaturated fatty acid, C22:5w6 is produced by some of the strains, including all of the prior art strains (up to a ratio of 1:4 with the C22:6w3 fatty acid). However, C22:5w6 fatty acid is considered undesirable as a dietary fatty acid because it can retroconvert to the C20:4w6 fatty acid. The screening procedure outlined in this invention, however, facilitates the isolation of some strains that contain no (or less than 1%) omega-6 highly unsaturated fatty acids (C20:4w6 or C22:5w6).

HUFAs in microbial products, such as those produced by the present process, when exposed to oxidizing conditions can be converted to less desirable unsaturated fatty acids or to saturated fatty acids. However, saturation of omega-3 HUFAs can be reduced or prevented by the introduction of synthetic antioxidants or naturally-occurring antioxidants, such as beta-carotene, vitamin E and vitamin C, into the microbial products.

Synthetic antioxidants, such as BHT, BHA, TBHQ or ethoxyquin, or natural antioxidants such as tocopherol, can be incorporated into the food or feed products by adding them to the products during processing of the cells after harvest. The amount of antioxidants incorporated in this manner depends, for example, on subsequent use requirements, such as product formulation, packaging methods, and desired shelf life.

Concentrations of naturally-occurring antioxidants can be manipulated by harvesting a fermentation in stationary phase rather than during exponential growth, by stressing a fermentation with low temperature, and/or by maintaining a high dissolved oxygen concentration in the medium. Additionally, concentrations of naturally occurring antioxidants can be controlled by varying culture conditions such as temperature, salinity, and nutrient concentrations. Additionally, biosynthetic precursors to vitamin E, such as L-tyrosine or L-phenylalanine, can be incorporated into fermentation medium for uptake and subsequent conversion to vitamin E. Alternatively, compounds which act synergistically with antioxidants to prevent oxidation (e.g., ascorbic acid, citric acid, phosphoric acid) can be added to the fermentation for uptake by the cells prior to harvest. Additionally, concentrations of trace metals, particularly those that exist in two or more valency states, and that possess suitable oxidation-reduction potential (e.g., copper, iron, manganese, cobalt, nickel) should be maintained at the minimum needed for optimum growth to minimize their potential for causing autoxidation of the HUFAs in the processed cells.

Other products that can be extracted from the harvested cellular biomass include: protein, carbohydrate, sterols, carotenoids, xanthophylls, and enzymes (e.g., proteases). Strains producing high levels of omega-6 fatty acids have also been isolated. Such strains are useful for producing omega-6 fatty acids which, in turn, are useful starting materials for chemical synthesis of prostaglandins and other eicosanoids. Strains producing more than 25% of total fatty acids as omega-6 fatty acids have been isolated by the method described herein.

In one embodiment of the present invention, a harvested biomass can be dried (e.g., spray drying, tunnel drying, vacuum drying, or a similar process) and used as a feed or food supplement for any animal whose meat or products are consumed by animals. Similarly, extracted omega-3 HUFAs can be used as a feed or food supplement. Alternatively, the harvested and washed biomass can be used directly (without drying) as a feed supplement. To extend its shelf life, the wet biomass can be acidified (approximate pH=3.5–4.5) and/or pasteurized or flash heated to inactivate enzymes and then canned, bottled or packaged under a vacuum or non-oxidizing atmosphere (e.g., $N_2$ or $CO_2$).

The term "animal" means any organism belonging to the kingdom Animalia. Preferred animals from which to produce a food product include any economic food animal. More preferred animals include animals from which eggs, milk products, poultry meat, seafood, beef, pork or lamb is derived. Milk products include, for example, milk, cheese and butter. According to the present invention, "milk" refers to a mammary gland secretion of an animal which forms a natural food for animals. Seafood is derived from, without limitation, fish, shrimp and shellfish. When fed to such animals, omega-3 HUFAs in the harvested biomass or extracted omega-3 HUFAs are incorporated into the flesh, eggs or milk products of such animals to increase the omega-3 HUFA content thereof.

Preferred animals for milk product production include milk-producing animal, in particular cows, sheep, goats, bison, buffalo, antelope, deer and camels. More preferred animals for milk product production include cows, sheep and goats.

Methods to feed omega-3 HUFA-containing material to an animal that is a ruminant (i.e., cow, sheep or goat) can require some encapsulation technique for to protect the omega-3 HUFAs from breakdown or saturation by the rumen microflora prior to digestion and absorption of the omega-3 HUFAs by the animal. The omega-3 HUFA's can be "protected" by coating the oils or cells with a protein (e.g., zeain) or other substances which cannot be digested (or are poorly digested) in the rumen. This allows the fatty acids to pass undamaged through the ruminant's first stomach. The protein or other "protectant" substance is dissolved in a solvent prior to coating the cells or oil. The cells can be pelleted prior to coating with the protectant. Animals having high feed conversion ratios (e.g., 4:1–6:1) will require higher concentrations of omega-3 HUFAs to achieve an equivalent incorporation of omega-3 HUFAs as animal with low feed conversion ratios (2:1–3:1). Feeding techniques can be further optimized with respect to the period of an animal's life that harvested biomass or extracted omega-3 HUFAs must be fed to achieve a desired result.

Other methods to protect an omega-3 HUFA from degradation in a rumin include, for example, methods disclosed in U.S. Pat. No. 4,957,748, by Winowiski, issued Sep. 18, 1990; U.S. Pat. No. 5,023,091, by Winowiski, issued Jun. 11, 1991; and U.S. Pat. No. 5,064,665, by Winowiski, issued Nov. 12, 1991, all of which are incorporated herein by this reference in their entirety.

For most feed applications, the oil content of the harvested cells will be approximately 25–50% afdw, the remaining material being protein and carbohydrate. The protein can contribute significantly to the nutritional value of the cells as several of the strains that have been evaluated have all of the essential amino acids and would be considered a nutritionally balanced protein.

In a preferred process, the freshly harvested and washed cells (harvested by belt filtration, rotary drum filtration, centrifugation, etc.) containing omega-3 HUFAs can be mixed with any dry ground grain in order to lower the water content of the harvested cell paste to below 40% moisture. For example, corn can be used and such mixing will allow the cell paste/corn mixture to be directly extruded, using common extrusion procedures. The extrusion temperatures and pressures can be modified to vary the degree of cell rupture in the extruded product (from all whole cells to 100% broken cells). Extrusion of the cells in this manner does not appear to greatly reduce the omega-3 HUFA content of the cells, as some of the antioxidants in the grain may help protect the fatty acids from oxidation, and the extruded matrix may also help prevent oxygen from readily reaching the fatty acids. Synthetic or natural antioxidants can also be added to the cell paste/grain mixture prior to extrusion. By directly extruding the cell paste/grain mixture, drying times and costs can be greatly reduced, and it allows manipulation of the bioavailability of the omega-3 HUFAs for feed supplement applications by degree of cell rupture. The desired degree of cell rupture will depend on various factors, including the acceptable level of oxidation (increased cell rupture increases likelihood of oxidation) and the required degree of bioavailability by the animal consuming the extruded material.

The unicellular fungal strains isolated by the method described readily flocculate and settle, and this process can be enhanced by adjusting the pH of the culture to pH $\leq 7.0$. A 6-fold concentration of the cells within 1–2 minutes can be facilitated by this process. The method can therefore be employed to preconcentrate the cells prior to harvesting, or to concentrate the cells to a very high density prior to nitrogen limitation. Nitrogen limitation (to induce higher lipid production) can therefore be carried out in a much smaller reactor, or the cells from several reactors consolidated into one reactor.

A variety of procedures can be employed in the recovery of the microbial cells from the culture medium with preferred recovery processes being disclosed in U.S. Pat. No. 5,340,594, issued Aug. 23, 1994, which is incorporated herein by this reference in its entirety. In a preferred process, a mixture of high purity omega-3 HUFAs or high purity HUFAs can be easily concentrated from the extracted oils. The harvested cells (fresh or dried) can be ruptured or permeabilized by well-known techniques such as sonication, liquid-shear disruption methods (e.g., French press of Manton-Gaulin homogenizer), bead milling, pressing under high pressure, freeze-thawing, freeze pressing, or enzymatic digestion of the cell wall. The lipids from the ruptured cells are extracted by use of a solvent or mixture of solvents such as hexane, chloroform, ether, or methanol. The solvent is removed (for example by a vacuum rotary evaporator, which allows the solvent to be recovered and reused) and the lipids hydrolyzed by using any of the well-known methods for converting triglycerides to free fatty acids or esters of fatty acids including base hydrolysis, acid hydrolysis, or enzymatic hydrolysis. The hydrolysis should be carried out at as low a temperature as possible (e.g., room temperature to 60° C.) and under nitrogen to minimize breakdown of the omega-3 HUFAs. After hydrolysis is completed, the nonsaponifiable compounds are extracted into a solvent such as ether, hexane or chloroform and removed. The remaining solution is then acidified by addition of an acid such as HCl, and the free fatty acids extracted into a solvent such as hexane, ether, or chloroform. The solvent solution containing the free fatty acids can then be cooled to a temperature low enough for the non-HUFAs to crystallize, but not so low that HUFAs crystallize. Typically, the solution is cooled to between about −60° C. and about −74° C. The crystallized fatty acids (saturated fatty acids, and mono-, di-, and trienoic fatty acids) can then be removed (while keeping the solution cooled) by filtration, centrifugation or settling. The HUFAs remain dissolved in the filtrate (or supernatant). The solvent in the filtrate (or supernatant) can then be removed leaving a mixture of fatty acids which are >90% purity in either omega-3 HUFAs or HUFAs which are greater than or equal to 20 carbons in length. The purified omega-3 highly unsaturated fatty acids can then be used as a nutritional supplement for humans, as a food additive, or for pharmaceutical applications. For these uses the purified fatty acids can be encapsulated or used directly. Antioxidants can be added to the fatty acids to improve their stability.

The advantage of this process is that it is not necessary to go through the urea complex process or other expensive extraction methods, such as supercritical $CO_2$ extraction or high performance liquid chromatography, to remove saturated and mono-unsaturated fatty acids prior to cold crystallization. This advantage is enabled by starting the purification process with an oil consisting of a simple fatty acid profile such as that produces by Thraustochytrids (3 or 4 saturated or monounsaturated fatty acids with 3 or 4 HUFAs, two groups of fatty acids widely separated in terms of their crystallization temperatures) rather than a complex oil such as fish oil with up to 20 fatty acids (representing a continuous range of saturated, mono-, di-, tri-, and polyenoic fatty acids, and as such, a series of overlapping crystallization temperatures).

In a preferred process, the omega-3 HUFA enriched oils can be produced through cultivation of strains of the genus Thraustochytrium. After the oils are extracted from the cells by any of several well-known methods, the remaining extracted (lipids removed) biomass which is comprised mainly of proteins and carbohydrates, can be sterilized and returned to the fermenter, where the strains of Thraustochytrium can directly recycle it as a nutrient source (source of carbon and nitrogen). No prehydrolysis or predigestion of the cellular biomass is necessary. Extracted biomass of the genus Schizochytrium can be recycled in a similar manner if it is first digested by an acid and/or enzymatic treatment.

As discussed in detail above, the whole-cell biomass can be used directly as a food additive to enhance the omega-3 highly unsaturated fatty acid content and nutritional value of processed foods for human intake or for animal feed. When used as animal feed, omega-3 HUFAs are incorporated into the flesh or other products of animals. The complex lipids containing these fatty acids can also be extracted from the whole-cell product with solvents and utilized in a more concentrated form (e.g., encapsulated) for pharmaceutical or nutritional purposes and industrial applications. A further aspect of the present invention includes introducing omega-3 HUFAs from the foregoing sources into humans for the treatment of various diseases. As defined herein, "treat" means both the remedial and preventative practice of medicine. The dietary value of omega-3 HUFAs is widely recognized in the literature, and intake of omega-3 HUFAs produced in accordance with the present invention by humans is effective for treating cardiovascular diseases, inflammatory and/or immunological diseases and cancer.

The present invention is further defined in more detail by way of working examples described in related U.S. patent application Ser. No. 08/292,736, filed Aug. 8, 1994, which is incorporated herein by this reference in its entirety. Species meeting the selection criteria described above have not been described in the prior art. By employing these selection criteria, the inventor isolated over 25 potentially promising strains from approximately 1000 samples screened. Out of the approximate 20,500 strains in the American Type Culture Collection (ATCC), 10 strains were later identified as belonging to the same taxonomic group as the strains isolated by the inventor. Those strains still viable in the Collection were procured and used to compare with strains isolated and cultured by the disclosed procedures. The results of this comparison are presented in Examples 5 and 6 of U.S. Pat. No. 5,340,594.

Recent developments have resulted in revision of the taxonomy of the Thraustochytrids. The most recent taxonomic theorists place them with the algae. However, because of the continued taxonomic uncertainty, it would be best for the purposes of the present invention to consider the strains as Thraustochytrids (Order: Thraustochytriales; Family: Thraustochytriaceae; Genus: Thraustochytrium or Schizochytrium). The most recent taxonomic changes are summarized below.

All of the strains of unicellular microorganisms disclosed and claimed herein are members of the order Thraustochytriales. Thraustochytrids are marine eukaryotes with a rocky taxonomic history. Problems with the taxonomic placement of the Thraustochytrids have been reviewed most recent by Moss (1986), Bahnweb and Jackle (1986) and Chamberlain and Moss (1988). For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids retained in the Oomycetes (the biflagellate zoosporic fungi). It was initially assumed that the Oomycetes were related to the heterokont algae, and eventually a wide range of ultrastructural and biochemical studies, summarized by Barr (1983) supported this assumption. The Oomycetes were in fact accepted by Leedale (1974) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis (1970); e.g., mitochondria were derived from bacterial endosymbionts, chloroplasts from cyanophytes, and flagella from spirochaetes). The other theory suggests a gradual evolution of the membrane-bound organelles from the non-membrane-bounded systems of the prokaryote ancestor via an autogenous process (Cavalier-Smith 1975). Both groups of evolutionary biologists however, have removed the Oomycetes and thraustochytrids from the fungi and place them either with the chromophyte algae in the kingdom Chromophyta (Cavalier-Smith 1981) or with all algae in the kingdom Protoctista (Margulis and Sagan (1985).

With the development of electron microscopy, studies on the ultrastructure of the zoospores of two genera of Thraustochytrids, Thraustochytrium and Schizochytrium, (Perkins 1976; Kazama 1980; Barr 1981) have provided good evidence that the Thraustochytriaceae are only distantly related to the Oomycetes. Additionally, more recent genetic data representing a correspondence analysis (a form of multivariate statistics) of 5S ribosomal RNA sequences indicate that Thraustochytriales are clearly a unique group of eukaryotes, completely separate from the fungi, and most closely related to the red and brown algae, and to members of the Oomycetes (Mannella et al. 1987). Recently however, most taxonomists have agreed to remove the Thraustochytrids from the Oomycetes (Bartnicki-Garcia 1988).

In summary, employing the taxonomic system of Cavalier-Smith (1981, 1983), the Thraustochytrids are classified with the chromophyte algae in the kingdom Chromophyta, one of the four plant kingdoms. This places them in a completely different kingdom from the fungi, which are all placed in the kingdom Eufungi. The taxonomic placement of the Thraustochytrids is therefore summarized below:

Kingdom: Chromophyta

Phylum: Heterokonta

Order: Thraustochytriales

Family: Thraustochytriaceae

Genus: Thraustochytrium or Schizochytrium

Despite the uncertainty of taxonomic placement within higher classifications of Phylum and Kingdom, the Thraustochytrids remain a distinctive and characteristic grouping whose members remain classifiable within the order Thraustochytriales.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A milk product derived from an animal raised by feeding said animal a feed material, wherein said feed material comprises cultured microbial organisms containing omega-3 highly unsaturated fatty acid in an amount effective to increase the content of omega-3 highly unsaturated fatty acid in said milk product.

2. The milk product of claim 1, wherein said cultured microbial organisms have a higher average amount of omega-3 highly unsaturated fatty acid than an average for naturally-occurring organisms of a same genus.

3. The milk product of claim 1, wherein said milk product is selected from the group consisting of milk, cheese and butter.

4. The milk product of claim 1, wherein said animal is selected from the group consisting of cows, sheep, goats, bison, buffalo, antelope, deer and camels.

5. The milk product of claim 1, wherein said animal is selected from the group consisting of cows, sheep and goats.

6. The milk product of claim 1, wherein said feed material is protected from degradation in a rumen of said animal.

7. The milk product of claim 6, wherein said feed material is coated with a protein.

8. The milk product of claim 1, wherein said feed material comprises an element selected from the group consisting of Thraustochytriales, omega-3 highly unsaturated fatty acid extracted from Thraustochytriales, and mixtures thereof.

9. The milk product of claim 8, wherein said feed material comprises microorganisms of the genus Thraustochytrium, Schizochytrium or a mixture thereof in whole cell form.

10. The milk product of claim 8, wherein said Thraustochytriales is obtained by a direct fermentation of grain, corn syrup or agricultural/fermentation byproducts by Thraustochytrium, Schizochytrium or a mixture thereof.

11. The milk product of claim 10, wherein said grain is selected from the group consisting of corn, sorghum, rice, wheat, oats, rye and millet.

12. The milk product of claim 8, wherein said feed material further comprises a dry ground grain.

13. The milk product of claim 12, wherein said feed material contains less than about 40% water.

14. The milk product of claim 12, wherein said feed material is prepared by extrusion.

15. The milk product of claim 1, wherein said feed material contains omega-6 highly unsaturated fatty acid in an amount effective to increase the content of omega-6 highly unsaturated fatty acid in said milk product.

16. The milk product of claim 1, wherein said milk product is consumable by humans.

17. A milk product derived from an animal raised by feeding said animal a feed material comprising an element selected from the group consisting of Thraustochytriales, omega-3 highly unsaturated fatty acid extracted from Thraustochytriales, and mixtures thereof in an amount effective to increase the content of omega-3 highly unsaturated fatty acid in said milk product.

18. The milk product of claim 17, wherein said feed material comprises microorganisms of the genus Thraustochytrium, Schizochytrium or a mixture thereof in whole cell form.

19. The milk product of claim 17, wherein said Thraustochytriales is obtained by a direct fermentation of grain, corn syrup or agricultural/fermentation byproducts by Thraustochytrium, Schizochytrium or a mixture thereof.

20. The milk product of claim 19, wherein said grain is selected from the group consisting of corn, sorghum, rice, wheat, oats, rye and millet.

21. The milk product of claim 17, wherein said milk product is selected from the group consisting of milk, cheese and butter.

22. The milk product of claim 17, wherein said animal is selected from the group consisting of cows, sheep and goats.

23. A milk product derived from an animal raised by feeding said animal a feed material comprising an element selected from the group consisting of Thraustochytrium, Schizochytrium, omega-3 highly unsaturated fatty acid extracted from said Schizochytrium, omega-3 highly unsaturated fatty acid extracted from said Thraustochytrium, and mixtures thereof in an amount effective to increase the content of omega-3 highly unsaturated fatty acid in said milk product, wherein said milk product is selected from the group consisting of milk, cheese and butter, and wherein said animal is selected from the group consisting of cows, sheep and goats.

* * * * *

(12) EX PARTE REEXAMINATION CERTIFICATE (8804th)
United States Patent
Barclay

(10) Number: US 5,985,348 C1
(45) Certificate Issued: Jan. 17, 2012

(54) MILK PRODUCTS HAVING HIGH CONCENTRATION OF OMEGA-3 HIGHLY UNSATURATED FATTY ACIDS

(75) Inventor: William R. Barclay, Boulder, CO (US)

(73) Assignee: Martek Biosciences Corporation, Columbia, MD (US)

Reexamination Request:
No. 90/011,356, Dec. 20, 2010

Reexamination Certificate for:
Patent No.: 5,985,348
Issued: Nov. 16, 1999
Appl. No.: 08/918,325
Filed: Aug. 26, 1997

Related U.S. Application Data

(62) Division of application No. 08/483,477, filed on Jun. 7, 1995, now Pat. No. 5,698,244.

(51) Int. Cl.
*A23C 9/00* (2006.01)
*A23C 9/20* (2006.01)
*A23K 1/00* (2006.01)
*A23K 1/16* (2006.01)
*A23K 1/18* (2006.01)

(52) U.S. Cl. ............................... 426/580; 426/2; 426/53; 426/635

(58) Field of Classification Search .................. None
See application file for complete search history.

(56) References Cited

To view the complete listing of prior art documents cited during the proceeding for Reexamination Control Number 90/011,356, please refer to the USPTO's public Patent Application Information Retrieval (PAIR) system under the Display References tab.

*Primary Examiner* — Evelyn Huang

(57) ABSTRACT

A process for the heterotrophic or predominantly heterotrophic production of whole-celled or extracted microbial products with a high concentration of omega-3 highly unsaturated fatty acids, producible in an aerobic culture under controlled conditions using biologically pure cultures of heterotrophic single-celled fungi microorganisms of the order Thraustochytriales. The harvested whole-cell microbial product can be added to processed foods as a nutritional supplement, or to fish and animal feeds to enhance the omega-3 highly unsaturated fatty acid content of products produced from these animals. The lipids containing these fatty acids can also be extracted and used in nutritional, pharmaceutical and industrial applications.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-23 are cancelled.

* * * * *